(12) United States Patent
Wensel et al.

(10) Patent No.: US 8,608,754 B2
(45) Date of Patent: *Dec. 17, 2013

(54) CLOT CAPTURE COIL

(75) Inventors: Jeffrey P. Wensel, Newport Beach, CA (US); Y. Pierre Gobin, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 505 days.

This patent is subject to a terminal disclaimer.

(21) Appl. No.: 11/982,735

(22) Filed: Oct. 31, 2007

(65) Prior Publication Data

US 2008/0294181 A1 Nov. 27, 2008

Related U.S. Application Data

(63) Continuation of application No. 10/234,588, filed on Sep. 3, 2002, now abandoned, which is a continuation of application No. 09/170,135, filed on Oct. 12, 1998, now Pat. No. 6,530,935, which is a continuation-in-part of application No. 08/723,619, filed on Oct. 2, 1996, now Pat. No. 5,895,398.

(60) Provisional application No. 60/011,070, filed on Feb. 2, 1996, provisional application No. 60/018,715, filed on May 31, 1996.

(51) Int. Cl.
A61B 17/24 (2006.01)

(52) U.S. Cl.
USPC .......................................................... 606/114

(58) Field of Classification Search
USPC ......... 606/113–115, 200, 110, 127, 128, 159, 606/191; 623/1.15, 1.2, 1.22
See application file for complete search history.

(56) References Cited

U.S. PATENT DOCUMENTS 3,868,956 A 3/1975 Alfidi et al.
3,996,938 A 12/1976 Clark, III
(Continued)

FOREIGN PATENT DOCUMENTS

DE 3203410 A1 11/1982
EP 0337918 B1 10/1989
(Continued)

OTHER PUBLICATIONS

European Search Report for EP 09 00 7311, dated Jul. 23, 2009, 5 pages.

(Continued)

*Primary Examiner* — Ryan Severson
*Assistant Examiner* — Jonathan W Miles
(74) *Attorney, Agent, or Firm* — Christie, Parker & Hale, LLP

(57) ABSTRACT

A clot and foreign body removal device is described which comprises a catheter with at least one lumen. Located within the catheter is a clot capture coil that is connected to an insertion mandrel. In one embodiment, the clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. In another embodiment the coil is a biphasic coil which changes shape upon heating or passing an electric current. Once the coil configuration has been established, the coil can be used to ensnare and corkscrew a clot in a vessel. A clot is extracted from the vessel by moving the clot capture coil and catheter proximally until the clot can be removed or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed.

5 Claims, 17 Drawing Sheets

(56) References Cited

U.S. PATENT DOCUMENTS

| | | | |
|---|---|---|---|
| 4,655,771 A | | 4/1987 | Wallsten |
| 4,706,671 A | * | 11/1987 | Weinrib ............... 606/159 |
| 4,873,978 A | | 10/1989 | Ginsburg |
| 4,969,891 A | | 11/1990 | Gewertz |
| 4,994,069 A | * | 2/1991 | Ritchart et al. ............ 606/191 |
| 4,998,539 A | | 3/1991 | Delsanti |
| 5,011,488 A | | 4/1991 | Ginsburg |
| 5,054,501 A | | 10/1991 | Chuttani et al. |
| 5,071,407 A | | 12/1991 | Termin et al. |
| 5,217,484 A | | 6/1993 | Marks |
| 5,256,146 A | | 10/1993 | Ensminger et al. |
| 5,382,259 A | * | 1/1995 | Phelps et al. ............... 606/151 |
| 5,490,859 A | * | 2/1996 | Mische et al. ............... 606/159 |
| 5,514,176 A | | 5/1996 | Bosley, Jr. |
| 5,522,819 A | * | 6/1996 | Graves et al. ............... 606/113 |
| 5,549,626 A | | 8/1996 | Miller et al. |
| 5,562,698 A | | 10/1996 | Parker |
| 5,688,234 A | | 11/1997 | Frisbie |
| 5,702,413 A | | 12/1997 | Lafontaine |
| 5,895,398 A | * | 4/1999 | Wensel et al. ............... 606/159 |
| 6,436,112 B2 | * | 8/2002 | Wensel et al. ............... 606/159 |
| 6,485,497 B2 | * | 11/2002 | Wensel et al. ............... 606/159 |
| 6,530,935 B2 | * | 3/2003 | Wensel et al. ............... 606/159 |
| 6,692,508 B2 | * | 2/2004 | Wensel et al. ............... 606/159 |
| 6,692,509 B2 | * | 2/2004 | Wensel et al. ............... 606/159 |
| 6,824,545 B2 | * | 11/2004 | Sepetka et al. ............... 606/113 |
| 2008/0262487 A1 | * | 10/2008 | Wensel et al. ............... 606/27 |

FOREIGN PATENT DOCUMENTS

| | | |
|---|---|---|
| EP | 0472368 B1 | 2/1992 |
| EP | 0473790 B1 | 3/1992 |
| GB | 2066668 A | 7/1981 |
| JP | 62-49841 | 3/1987 |
| JP | 2-11166 | 1/1990 |
| JP | 2-77245 | 3/1990 |
| JP | 5-137729 | 6/1993 |
| JP | 7-88192 | 4/1995 |
| JP | 7-124251 | 5/1995 |
| WO | WO 91/07928 | 6/1991 |
| WO | WO 95/25480 | 9/1995 |

OTHER PUBLICATIONS

Translation of Notice of Reasons for Rejection for Patent Application No. JP 9-527922, mailed Feb. 28, 2006, 8 pages.

Decision of Final Rejection for Patent Application No. JP 9-527922, mailed Jan. 30, 2007, 4 pages.

Notice of Reasons for Rejection for Patent Application No. JP 2007-146060, mailed Sep. 25, 2007, 5 pages.

Notice of Reasons for Rejection for Patent Application No. 2007-146060, mailed Apr. 22, 2008, 5 pages.

Decision for Rejection for Patent Application No. 2007-146060, mailed Nov. 25, 2008, 3 pages.

* cited by examiner

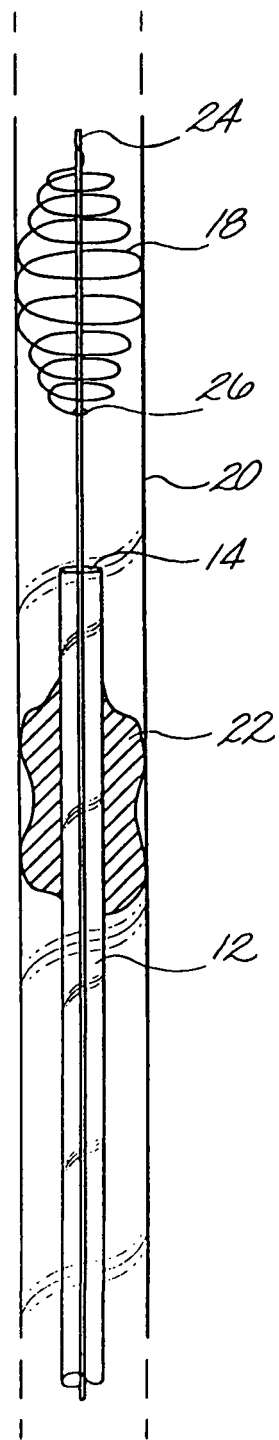

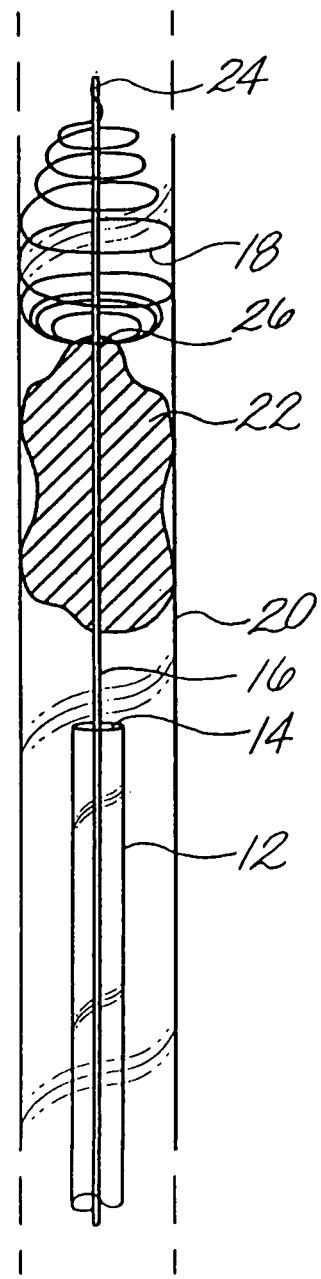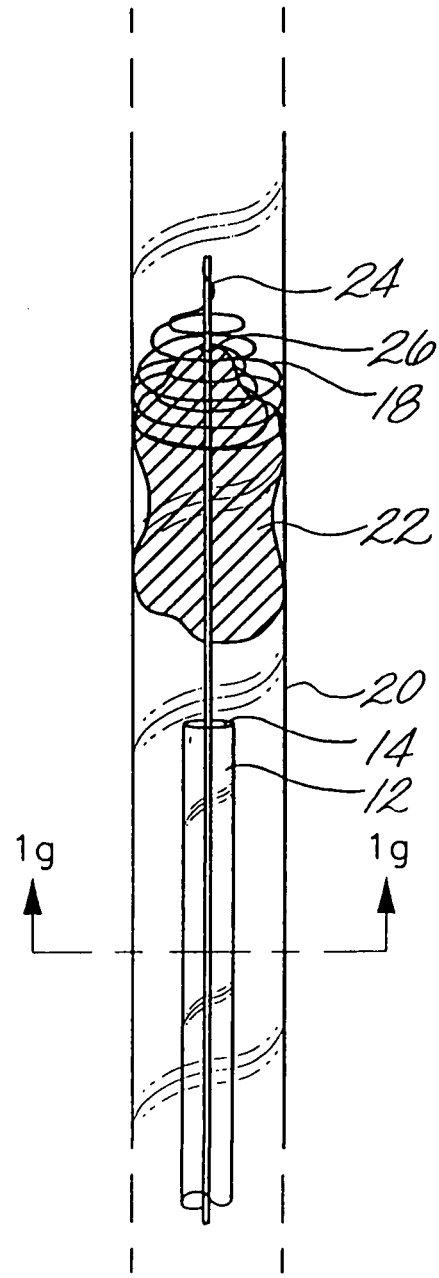

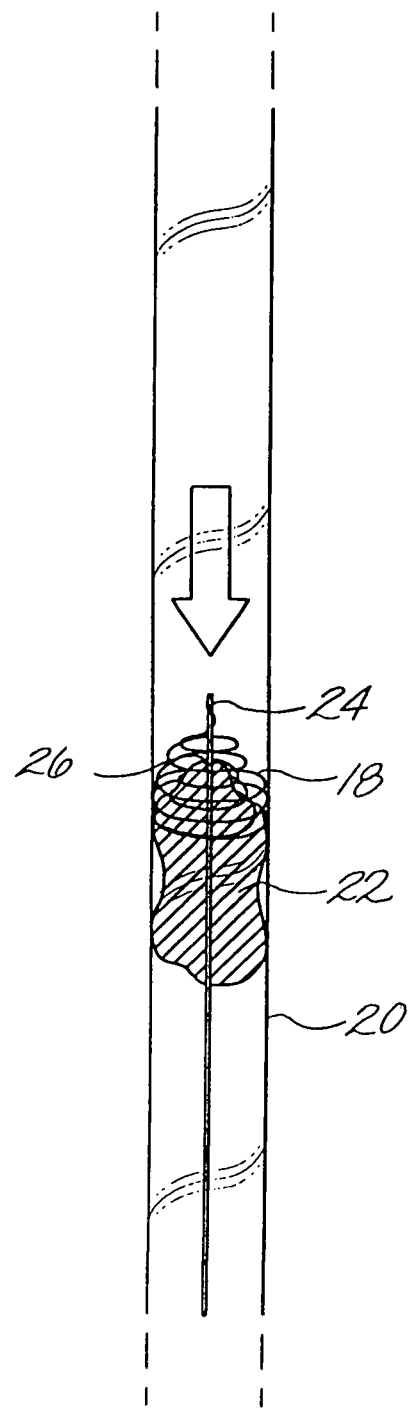

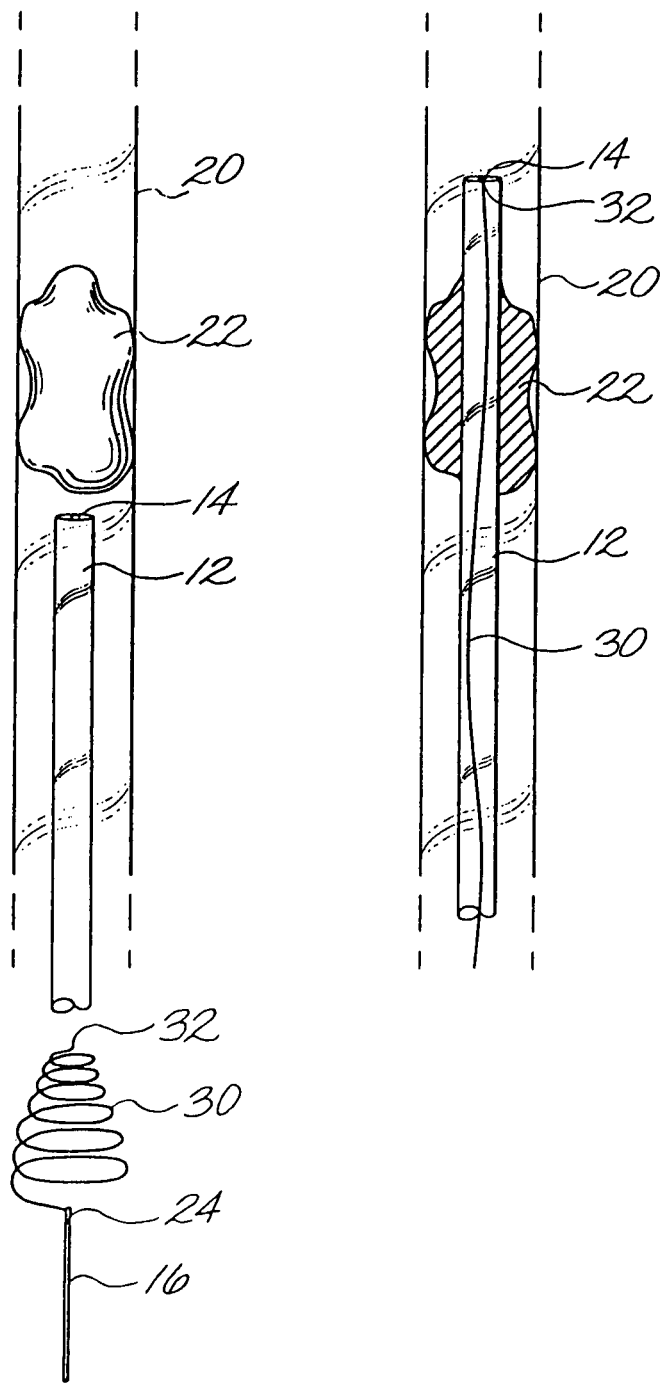

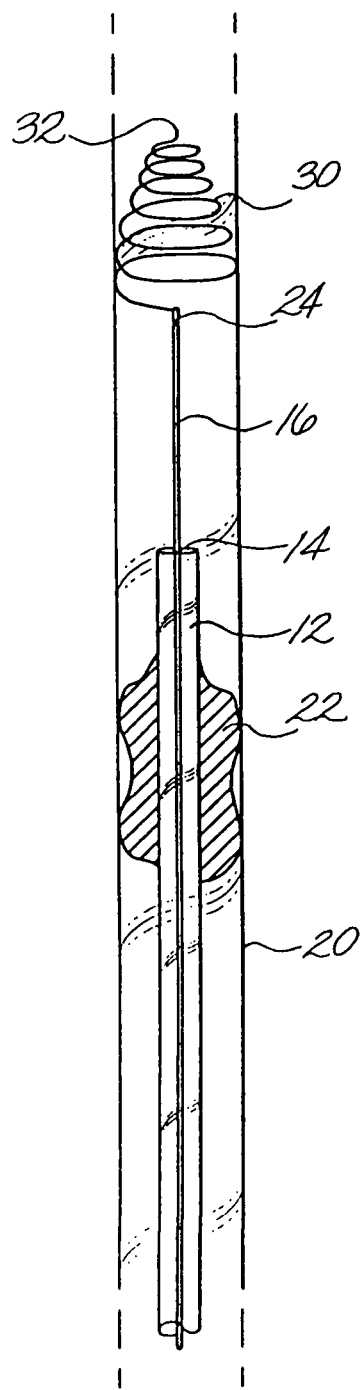
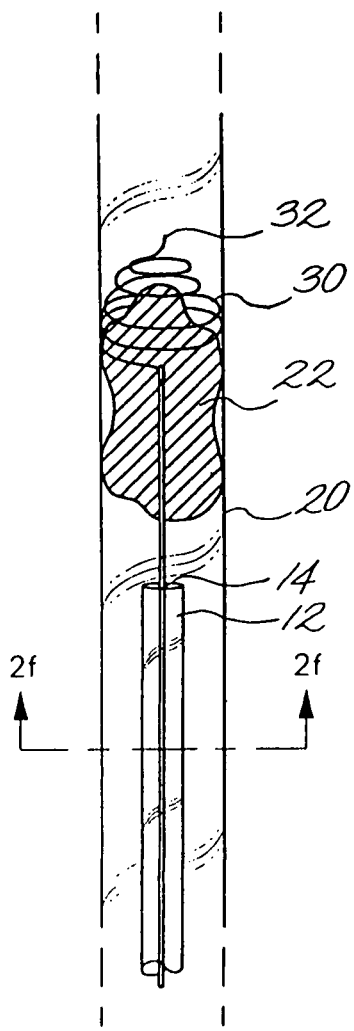

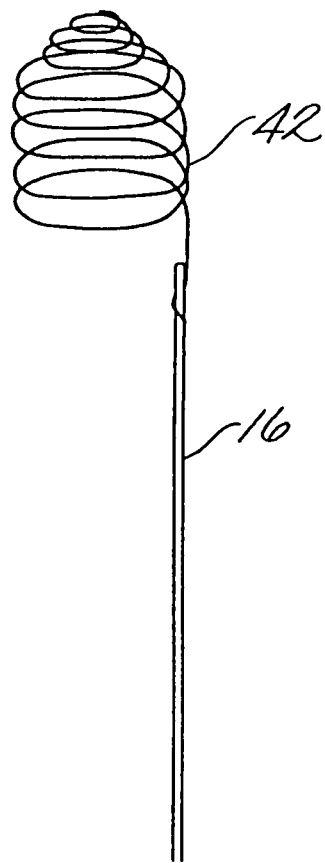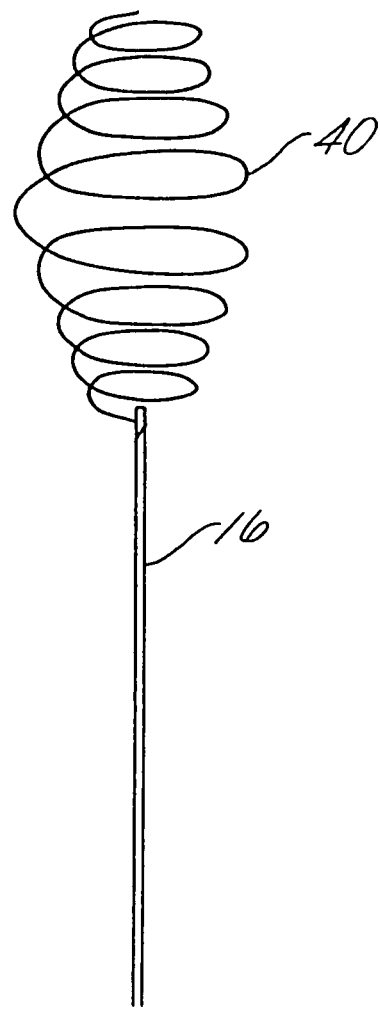
Fig. 6                    Fig. 7

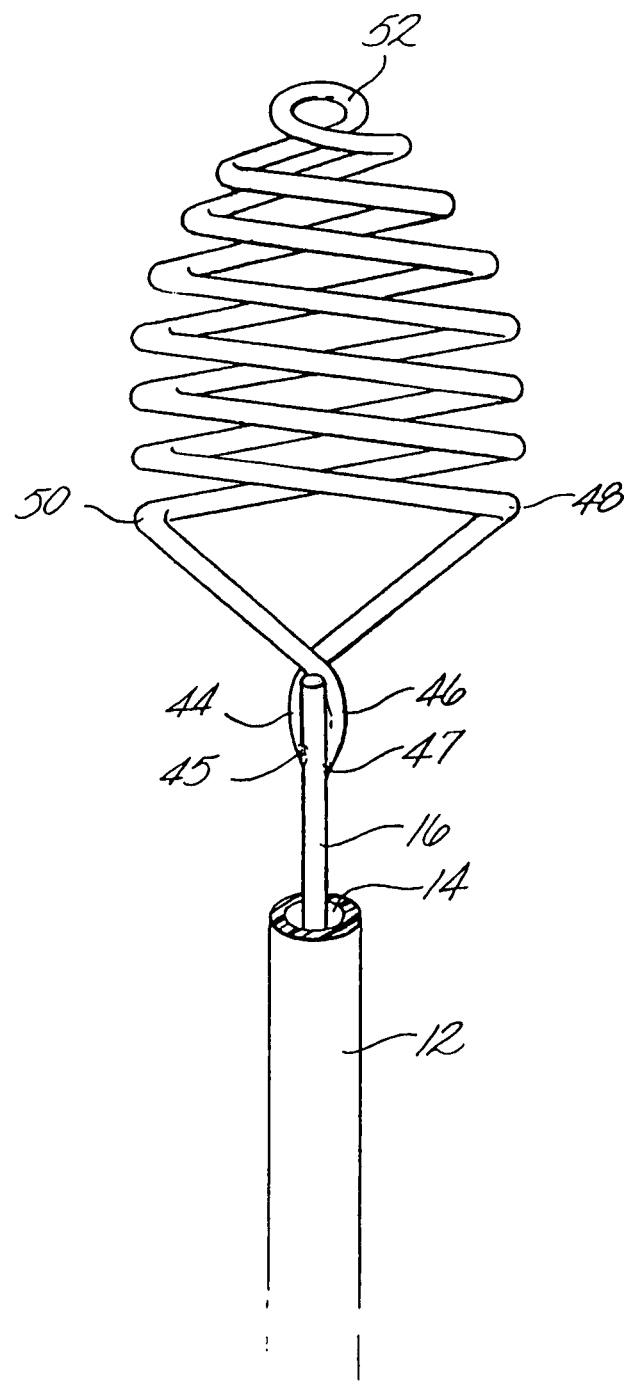

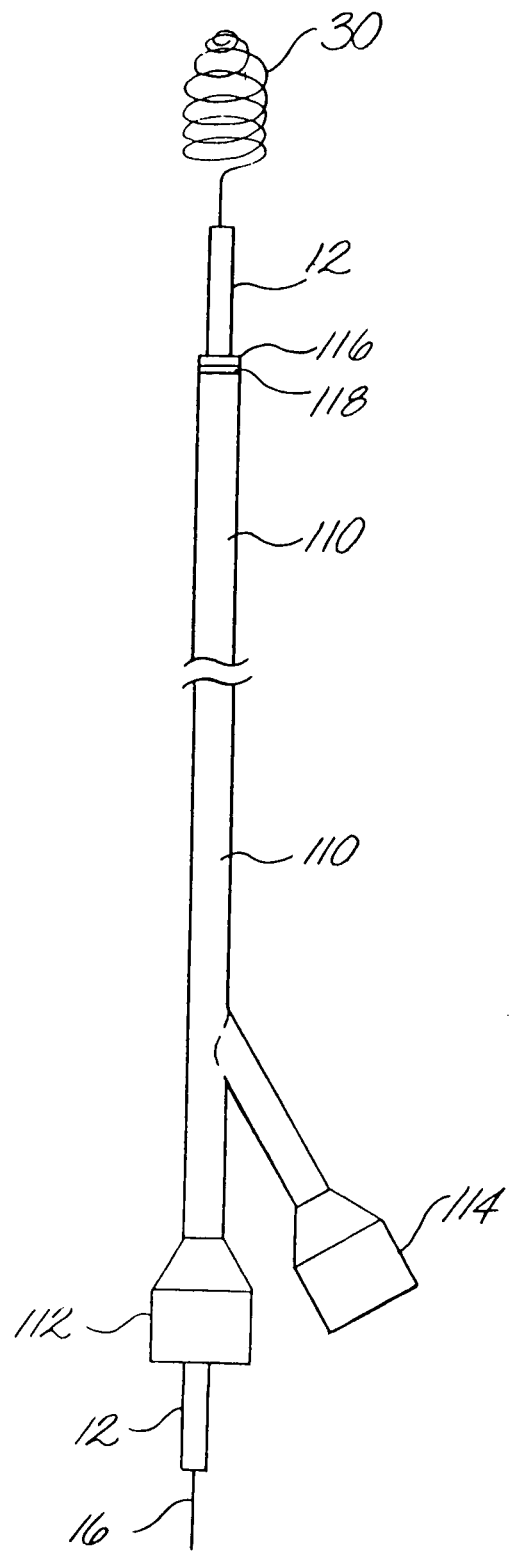

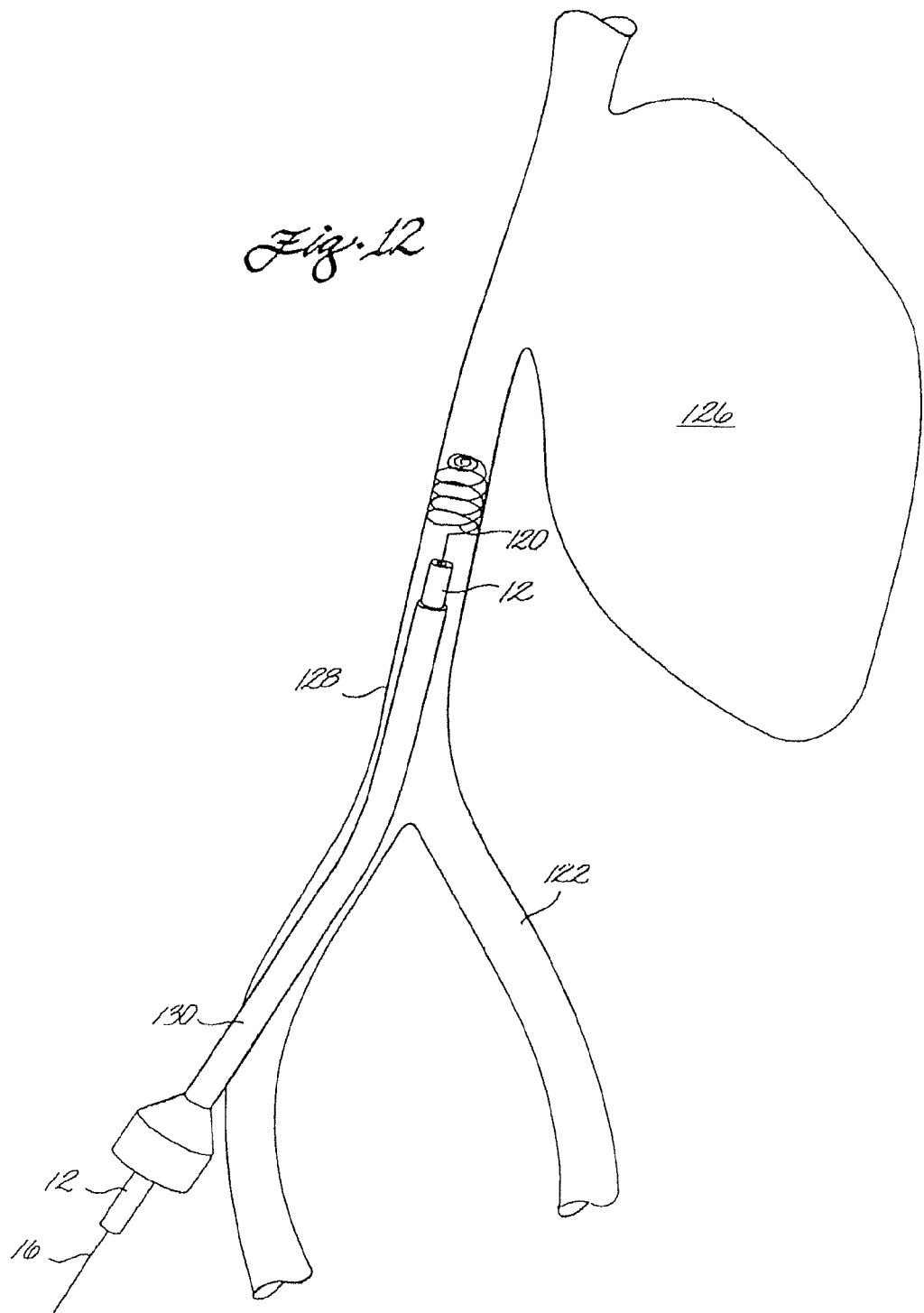

CLOT CAPTURE COIL

CROSS-REFERENCE TO RELATED APPLICATION(S)

This application is a continuation of U.S. patent application Ser. No. 10/234,588, filed Sep. 3, 2002, now abandoned, which is a continuation of Ser. No. 09/170,135, filed Oct. 12, 1998, now U.S. Pat. No. 6,530,935, which is a continuation-in-part of U.S. patent application Ser. No. 08/723,619, filed Oct. 2, 1996, now U.S. Pat. No. 5,895,398, which claims priority to U.S. Provisional Patent Application Ser. Nos. 60/011,070, filed Feb. 2, 1996, and 60/018,715, filed May 31, 1996, the disclosures of which are all incorporated by reference herein.

FIELD OF THE INVENTION

The present invention relates to medical devices that are useful in treating thromboembolic disorders and for removal of foreign bodies in the vascular system.

BACKGROUND OF THE INVENTION

Thromboembolic disorders, such as stroke, pulmonary embolism, peripheral thrombosis, atherosclerosis, and the like, affect many people. These disorders are a major cause of morbidity and mortality in the United States.

Thromboembolic events are characterized by an occlusion of a blood vessel. The occlusion is caused by a clot which is viscoelastic (jelly like) and is comprised of platelets, fibrinogen and other clotting proteins.

When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke or even death. Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as the Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and best avoided when possible. Additionally, the use of a Fogarty catheter is problematic because of the great risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel, typically through an introducing catheter. The balloon-tipped catheter is then advanced to the point of the occlusion and inflated in order to dilate the stenosis. Balloon angioplasty is appropriate for treating vessel stenosis but is not effective for treating acute thromboembolisms.

Another percutaneous technique is to place a microcatheter near the clot and infuse streptokinase, urokinase or other thrombolytic agents to dissolve the clot. Unfortunately, thrombolysis typically takes hours to days to be successful. Additionally, thrombolytic agents can cause severe hemorrhage and in many patients the agents cannot be used at all.

U.S. Pat. Nos. 4,706,671 and 5,011,488 both describe the use of a coiled section for the removal of thromboembolic material. However, neither patent describes a device that is marketed. U.S. Pat. No. 4,706,671 teaches the use of a hollow flexible elastomeric material to form the shape of the coiled section. The coiled section is hollow to allow for the insertion of a liquid into the hollow center such that the coils become stiff. U.S. Pat. No. 5,011,488 teaches the use of a coiled section that is fixed on both the proximal and distal ends such that the operator of the device can change the shape and size of the coils. However, this device may be impossible to manufacture and is impossible to use in small vessels.

Another problematic area is the removal of foreign bodies. Foreign bodies introduced into the circulation can be fragments of catheters, pace-maker electrodes, guide wires, and erroneously placed embolic material such as thrombogenic coils. The only available retrieval devices for the removal of foreign bodies are devices which form a loop that can ensnare the foreign material by decreasing the size of the diameter of the loop around the foreign body. The use of such removal devices is difficult and sometimes unsuccessful.

Thus, there exists a need for the development of a device that can be easily deployed into the circulatory system for the removal of viscoelastic clots and foreign bodies. There is also a need for a device which could be used as a temporary arterial or venous filter to capture and remove thromboemboli formed during endovascular procedures.

SUMMARY OF THE INVENTION

The present invention is a coil type device that is useful in removing clots and foreign bodies in vessels. The invention comprises a catheter with at least one lumen. Located within the catheter is a clot capture coil that is connected to an insertion mandrel. The clot capture coil is made out of a solid elastic or superelastic material which has shape memory. The elasticity or superelasticity of the coil allows it to be deformed within the catheter and then to reform its original coil configuration when the coil is moved outside of the catheter lumen.

In an alternate embodiment, the coil is made out of a biphasic material which changes shape upon heating or the passage of electrical current. The coil is straight initially, and then after passing electrical current or heat the coil changes to its coil configuration.

Once the coil configuration has been established, the coil can be used to ensnare and corkscrew a clot in a vessel. The clot is extracted from the vessel by moving the clot capture coil and catheter proximally until the clot can be removed or released into a different vessel that does not perfuse a critical organ. The coil can also be used as a temporary arterial or venous filter to capture and remove thromboemboli formed during endovascular procedures. Foreign bodies are captured by deploying the coil distal to the foreign body and moving the clot capture coil proximally until the foreign body is trapped within the coil. By removing the device from the body, the foreign material is also removed.

BRIEF DESCRIPTION OF THE DRAWINGS

Embodiments of the invention will now be described with reference to the following drawings wherein:

FIG. 1c is a schematic illustration of the deployment of the clot capture coil within an occluded artery;

FIG. 1d is a schematic illustration of the clot capture coil of the present invention encountering a clot in an occluded artery;

FIG. 1e is a schematic illustration of the clot capture coil ensnaring the clot in an occluded artery;

FIG. 1f is a schematic illustration of the clot of FIG. 1e being moved within an occluded artery via the clot capture coil;

FIG. 2a is a schematic illustration of an occluded artery and an alternate embodiment of the clot capture coil;

FIG. 2b is a schematic illustration of a microcatheter passed through a clot within an occluded artery and the extended coil of the clot capture coil within the catheter;

FIG. 2c is a schematic illustration of the deployment of the clot capture coil in an occluded artery;

FIG. 2d is a schematic illustration of a clot capture coil ensnaring a clot within an occluded artery;

FIG. 6 is an additional coil configuration;

FIG. 7 is a further coil configuration;

FIG. 8 is a double helix coil configuration and a single lumen catheter;

FIG. 10b is a schematic illustration of a clot capture coil straightened within the inner lumen of the introducer of FIG. 10a;

FIG. 11 is a plan view of the present invention being deployed within an introducing catheter with a side suction port;

FIG. 12 is a schematic view of the present invention being deployed within an introducing catheter such that the coil section is within the inferior vena cava of a patient;

DESCRIPTION OF THE PREFERRED EMBODIMENTS

Figure 1A:
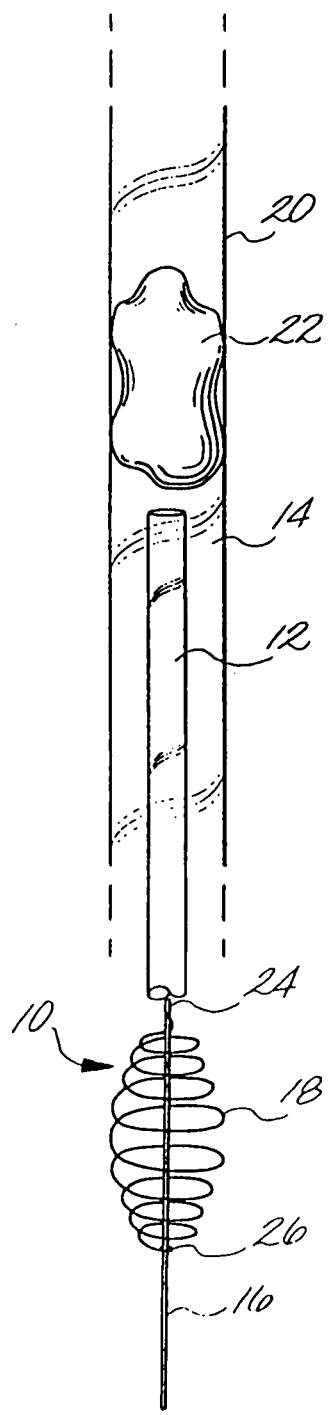
FIG. 1a is a schematic illustration of an occluded artery with a microcatheter and the clot capture coil of the present invention.
Figure 1B:
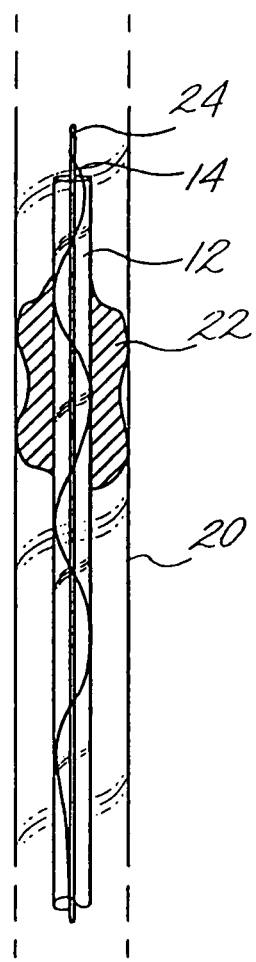
FIG. 1b is a schematic illustration of an occluded artery with a microcatheter and a clot capture coil inserted through an occlusion.
Figure 1G:
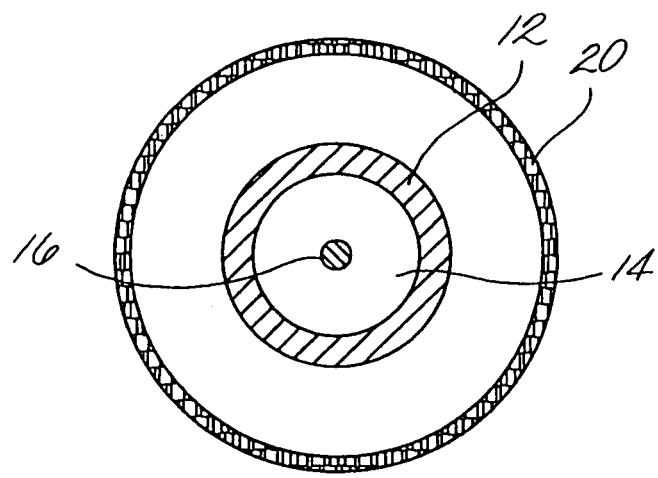
FIG. 1g is a cross section of the artery and the catheter of FIG. 1e along line 1g-1g.
Figure 2F:
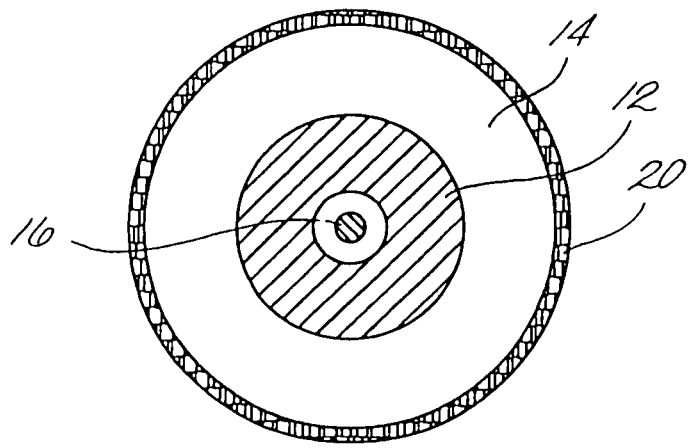
FIG. 2f is a cross section of the artery and catheter of FIG. 2d at line 2f-2f.
Figure 2E:
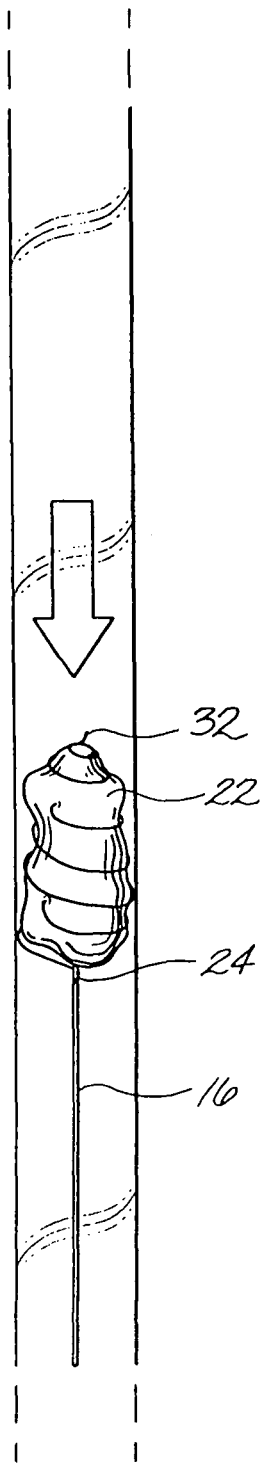
FIG. 2e is a schematic illustration of the removal of a clot via a clot capture coil illustrating the corkscrewing and ensnaring effect of the coil within the viscoelastic clot.

Turning now to FIGS. 1a-1g, a clot capture coil device 10 is generally illustrated within an artery 20 with a clot 22. The device comprises a catheter 12 with at least one lumen 14, a clot capture coil (an obstruction retriever having a solid, non-hollow, obstruction-engaging portion) 18, and an insertion mandrel (insertion element) 16.

The catheter 12 can be any commercially available catheter that is made out of any appropriate biologically compatible material. Typically, the catheter will have a single lumen 14 and is constructed out of a flexible elastomeric materials such as silicone, rubber, polyvinylchloride, polyurethanes, polyesters, polytetrafluoroethylene, and the like. The catheter has to be flexible enough and long enough to navigate through blood vessels to the occluded vessel 20 where clot 22 is located. Typically the catheter will range in length from about 20 to about 175 cm.

The outer diameter of the catheter can also vary. Typically the outer diameter will range from about 2 to about 10 French (one French=0.013 inch). The inner diameter will range from about 1 to about 9 French.

The insertion mandrel 16 has to be relatively stiff to support the coil 18. In the preferred embodiment, the insertion mandrel is made out of stainless steel and is a solid wire of from about 0.006 to about 0.038 inch in diameter. Other materials could be used such as a hard plastic, nitinol, and the like to make the insertion mandrel. The insertion mandrel is 10 to 20 cm longer than the catheter such that the operator of the device (typically a physician) can control the insertion mandrel by gripping the proximal end which extends from the proximal end of the catheter.

Connected to the insertion mandrel is the clot capture coil 18. In one embodiment, the coil is made from a flexible solid elastic or superelastic material which has shape memory, i.e., it can deform to a straight position and then return to a resting coil configuration. In a preferred embodiment, the coil is made out of a solid nitinol wire with a diameter of about 0.001 to about 0.038 inch. The use of nitinol in medical devices is well known in the art. Nitinol is preferred because of its superelasticity and its shape memory. However, other solid materials that are also elastic or superelastic and have shape memory could also be used such as some synthetic plastics, metallic alloys, and the like. To make the coil, the nitinol wire is wrapped around a mandrel into the coil configuration. The nitinol is then heated to an appropriate temperature such that the nitinol wire adopts the coil configuration as its resting shape upon cooling. The diameter of the coils can vary depending on the size of the vessel occluded. The diameter can range from about 1 mm for small vessels to about 30 mm for large vessels such as the pulmonary arteries or inferior vena cava. The length of the coil can also vary but typically ranges from about 3 to about 100 mm in the proximal to distal direction. Because the nitinol coil is superelastic, the coil can be extended to a completely straight configuration with the use of minimal force and then reform to its natural resting configuration when the force is removed. In use, the coil is extended by using the insertion mandrel to insert the coil and the mandrel into the narrow lumen of the catheter.

In another embodiment, the coil is made out of a solid biphasic material which changes shape upon heating or the passage of electric current. A presently preferred material is biphasic nitinol which has a straight configuration initially, and changes to a coiled configuration upon the passage of electric current or heating. The use of biphasic nitinol is well known in the medical arts for other purposes. The biphasic nitinol coil would be made using ordinary skill in the art such that the nitinol coil is straight initially and then forms the appropriate coil configuration. As would be apparent to a person skilled in the art, the biphasic coil could also be constructed such that the initial coil configuration is the normal shape and that the biphasic coil straightens upon passing electric current or heating. The coil dimensions would be similar to the dimension detailed above for the shape memory coil.

The coil section of either the shape memory coil or the biphasic coil can have many different configurations. Similar reference numerals are used throughout the figures to indicate similar components of the embodiments. In the embodiment illustrated in FIGS. 1a-1f, the coil is barrel-shaped such that the diameter of the coil is relatively small at the distal and proximal ends of the coil and is relatively large in the center of the coil. In a typical coil configuration, the diameter of the coil ranges from 2 mm at the proximal and distal ends and expands to 10 mm in the center. However, other sizes are also useful depending on the relative size of the occluded vessel. At the proximal end of the coil is a small circular loop 26. In the preferred illustrated embodiment, the circular loop is placed around the mandrel and is freely slidable over the mandrel. The distal end of the barrel-shaped coil is permanently connected to the distal end 24 of the insertion mandrel. Thus, in this embodiment the coil extends proximally from the distal end of the insertion mandrel. In the preferred embodiment the coil is welded onto the distal end of the insertion mandrel. Other means of permanently connecting the coil could also be used such as crimping the coil, gluing the coil, screwing the coil into a screw type mount, and the like.

A different coil configuration is illustrated in FIGS. 2a-2f. In this embodiment, the coil (obstruction retriever having a solid, non-hollow, obstruction-engaging portion) 30 is connected at its proximal end to the distal end 24 of the insertion mandrel (insertion element) 16. Thus, the coil extends distally from the distal end of the insertion mandrel. The distal end 32 of the coil is free floating. The coil is conically shaped with the diameter of the coils decreasing distally to the free end 32. Embodiments where the coil is connected to the proximal end are preferred for use in removing clots from small and/or tortuous vessels as will be discussed below.

Figure 3:
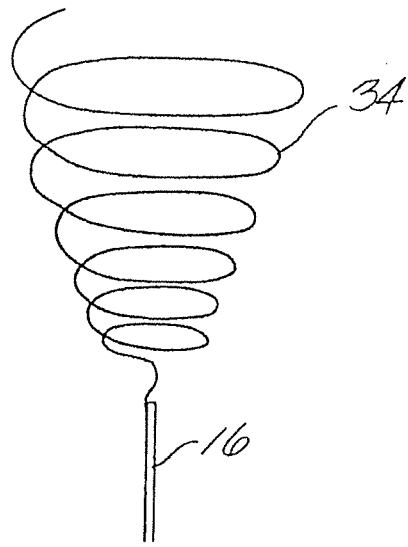
FIG. 3 is an alternate coil configuration.

The size and shape of the coils can vary and different representative embodiments are illustrated in the different figures. FIG. 3 illustrates an alternate embodiment where the coil 34 is attached at its proximal end to the distal end of the insertion mandrel 16. Thus, the coil extends distally away from the distal end of the insertion mandrel. The coil is shaped like an inverted cone with the diameter of the coils increasing distally. This embodiment is particularly useful for retrieving clots from small (1-2 mm diameter) vessels in the cerebral and coronary circulations. The diameter of the coils in this configuration are typically from about 1 mm to about 3 mm, could be larger depending on the relative size of the occluded vessel.

Figure 4:
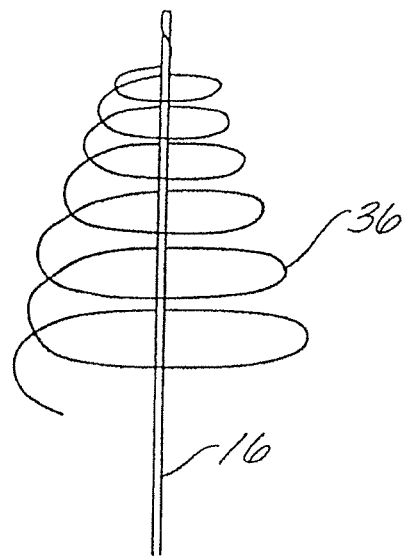
FIG. 4 is an alternate coil configuration.
Figure 5:
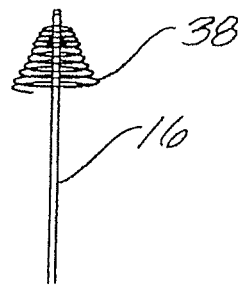
FIG. 5 is a further coil configuration.

FIG. 4 illustrates a cone-shaped coil 36 where the distal end of the coil is connected to the distal end of the insertion mandrel. FIG. 5 is a similar embodiment to FIG. 4 except that the coil 38 is wound tighter such that there are more revolutions per inch. In both FIGS. 4 and 5 the coil section extends proximally from the distal end of the insertion mandrel.

FIG. 6 illustrates a different embodiment where the proximal end of the coil 42 is connected to the insertion mandrel's distal end. The coil is shaped like an inverted cup which has a constant diameter until the coil reaches its most distal end where the diameter decreases.

FIG. 7 is a similar embodiment to FIGS. 1a-1f except that the barrel-shaped coil 40 is connected to the distal end of the insertion mandrel such that the coil extends distally instead of proximally.

The embodiment of FIG. 8 is a double helix coil configuration that is useful for large clot removal. The configuration is such that one continuous piece of wire is used to form the double helix configuration. Both ends of the coil 44 and 46 are connected to the distal end of the insertion mandrel 16. In the preferred embodiment, both ends are welded onto the insertion mandrel 16 at weld lines 45 and 47. The coil has been heat treated such that it forms a resting double helix shape. The two helixes 48 and 50 intertwine and are connected at the top of each helix at point 52. When the double helix coil is withdrawn into the single lumen catheter by translating the insertion mandrel, the helixes straighten until the coils are completely withdrawn into the catheter's lumen. By translating the insertion member in the opposite direction, the coil is forced out of the lumen of the catheter and then reforms the double helix configuration.

Figure 9:
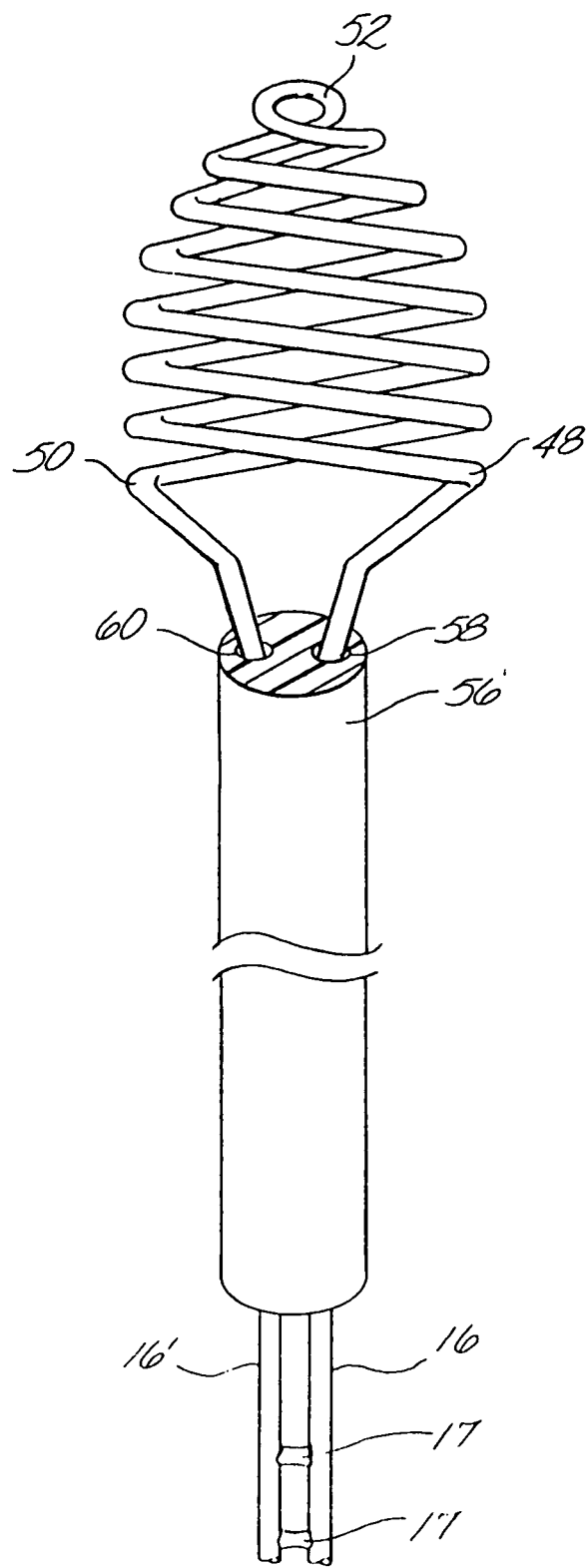
FIG. 9 is a double helix coil configuration and a double lumen catheter.

FIG. 9 is an alternate double helix embodiment where the double helix is used in conjunction with a double lumen catheter 56. The lumens 58 and 60 each receive an insertion mandrel 16 and 16'. Each insertion mandrel in turn is permanently connected to one of the ends of the coil. At the proximal end of the insertion mandrels are optional connecting bars 17 which keep the relative spacial relationship of each insertion mandrel constant. In this embodiment, as the helixes are withdrawn into the catheter, each one straightens out and is kept separate within the respective lumens. When the helixes are then deployed by translating the insertion mandrel, the helixes reform the double helix configuration. The optional connecting bars 17 are used to ensure that each helix is being deployed by the translation of the insertion mandrels and are in unison with each other such that the double helix configuration is always obtained upon full deployment.

Figure 13:
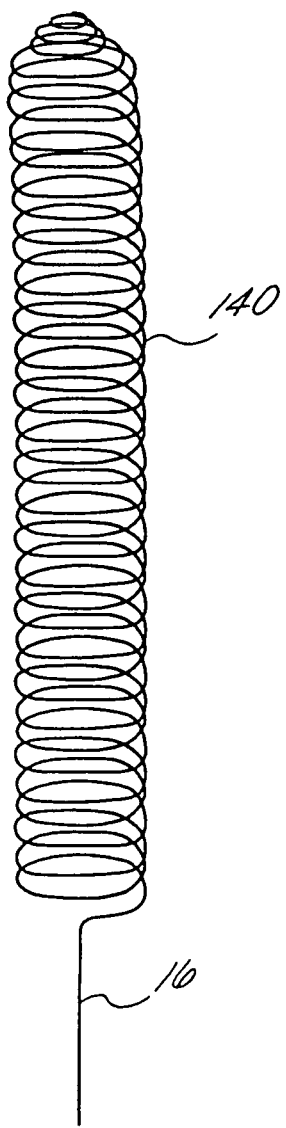
FIG. 13 is an alternate coil configuration that is particularly useful for removing clots in a surgically created arteriovenous fistula of a hemodialysis patient.

FIG. 13 illustrates a long coil 140, ranging from about 2 cm to about 10 cm that is especially useful for removing clots in a surgically created arteriovenous fistula of a hemodialysis patient. The coil could also be used for removing long clots in the venous system and long clots in a surgically created by-pass graft. The arteriovenous fistulas are normally surgically created on the forearm of a hemodialysis patient and allows for easy access to the blood stream for hemodialysis treatment. Unfortunately, these fistulas often become clogged with long blood clots and have to be surgically repaired or a new fistula created. The long clot capture coil 140 is connected to the insertion mandrel 16 at the coil's proximal end.

Figure 14:
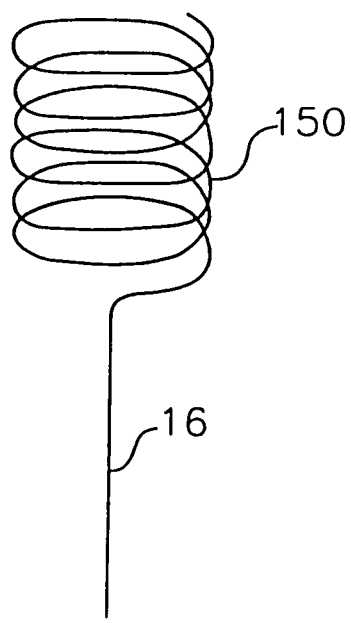
FIG. 14 is a further coil configuration.
Figure 15:
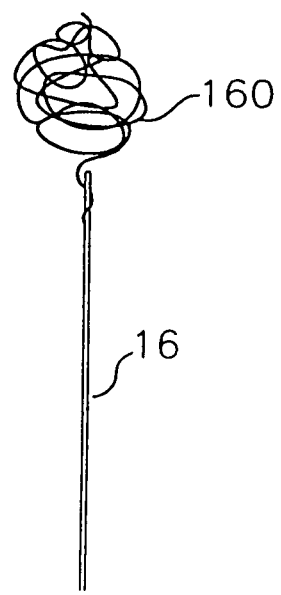
FIG. 15 is another coil configuration.

FIGS. 14 and 15 illustrate two further coil configurations. FIG. 14 is a cylindrical coil 150 attached to the distal end of the insertion mandrel 16. FIG. 15 is a random tangle coil attached to the insertion mandrel 16. The random tangle is manufactured by extruding the coil material in a random fashion. The random tangles made by such a process would vary each time the tangles are manufactured, and thus, the random tangle pictured in FIG. 15 is for illustration only.

In a preferred embodiment, part or all of the coil is either made of, or covered by, a radiopaque material to permit monitoring of the location of the coil using x-rays. In a particularly preferred embodiment, the distal tip of the coil is radiopaque. The coil can be made, for example, of gold or platinum, or anther radiopaque material. If the coil is made from nitinol, which is not radiopaque, the nitinol coil can be modified to make part or all of it radiopaque. For example, a microcoil of platinum, gold or other radiopaque material can be coiled around the distal tip of the nitinol coil. The radiopaque microcoil can alternatively be wrapped around any other part of the nitinol coil, or even around the entire coil.

Figure 10A:
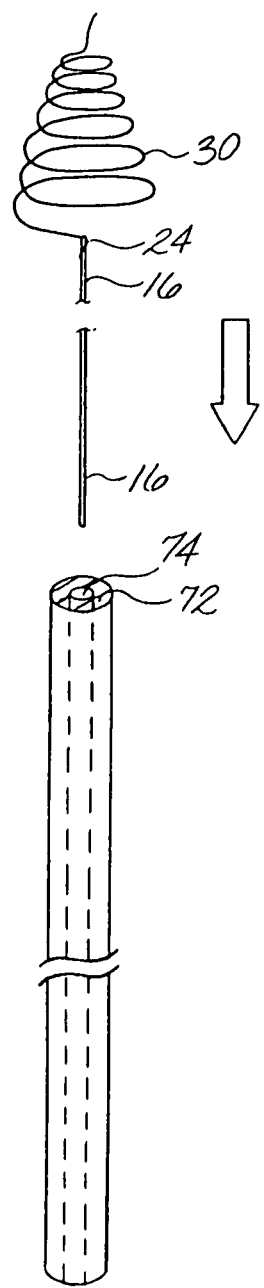
FIG. 10a is a schematic illustration of the clot capture coil and an introducer.
Figure 10B:
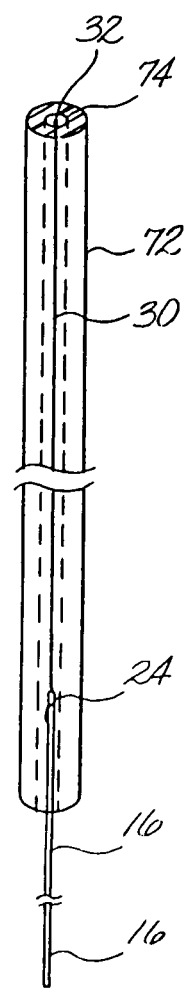

FIGS. 10a and 10b illustrate the use of an introducer 72 with lumen 74. The introducer is a relatively long (170 cm long) single lumen catheter that is used to straighten the coil section of a shape memory coil which extends distally, such as the coils in FIGS. 2, 3, 6, and 7, prior to insertion into the catheter 12 of the present invention. A longer introducer would be used for the arteriovenous fistula coil of FIG. 13. The insertion mandrel is inserted into the introducer in a retrograde direction (indicated by the arrow in FIG. 10a). Once the introducer reaches the shape memory coil section, the coil section straightens out almost to a complete straight line. In a coil section that extends distally outward, the inner diameter of the introducer and the catheter are sized to be just slightly larger than the diameter of the insertion mandrel and the coil section. That is, if the insertion mandrel and the coil are each made from 0.008 inch diameter wires, then the inner diameter of the introducer is preferably 1 to 2 French. Once the coil has been straightened out completely, the coil within the introducer is aligned with the catheter and then advanced in an anterograde direction into the catheter.

The above detailed description describes some of the numerous embodiments of the present invention. Below is a discussion of some of the numerous uses of the invention.

In use, a patient presenting symptoms of a thromboembolic disorder is examined radiographically using angiography to locate an occlusion and to confirm the diagnosis. A large introducing catheter 130 (see FIG. 12) is then inserted into an appropriate vessel (usually the femoral artery or the femoral vein). A small catheter or microcatheter 12 is then introduced into the vessel via the introducing catheter and advanced using a guide wire or the like into the occluded vessel. The catheter 12 is then passed through the viscoelastic clot. Once the catheter is in place and through the viscoelastic clot the clot capture coil is introduced into the catheter using the insertion mandrel and advanced to the distal tip of the catheter. For the shape memory clot capture coils that extend proximally from the insertion mandrel (as in FIGS. 1a-1f, the coil and the insertion mandrel are inserted directly into the proximal end of the catheter and advanced to the distal end (see FIG. 1b). For the shape memory clot capture coils that extend distally from the insertion mandrel (as in FIGS. 2a-2e), the introducer of FIGS. 10a and 10b is used as described above. For the biphasic coils, the coils are introduced in the straight configuration by either having the straight configuration the natural configuration or by straightening a natural coil configuration by passing electric current or heating the coil.

Once the catheter and the clot capture coil have transversed the clot, the insertion mandrel is translated distally relative to the catheter. With a shape memory coil, the coil deploys and reforms its natural configuration outside the distal end of the catheter. By comparing FIGS. 1c and 2c it is apparent that the shape memory coils which extend distally from the insertion mandrel immediately start to form the coil configuration once part of the coil is freed from the confines of the lumen of the catheter. These embodiments are particularly useful for clot removal in vessels that are small and/or tortuous where there is not much room for the advancement of the insertion mandrel and the coil. In the embodiments where the shape memory coil extends proximally from the distal end of the insertion mandrel, the entire length of the coil needs to be freed from the confines of the lumen of the catheter before it reforms the coil configuration. These embodiments are useful for the removal of large clots in large vessels because the coil is better supported and the coils can collapse upon each other. For example, as illustrated in FIGS. 1c-1f the proximal end of the coil which is a slidable loop 26 mounted around the insertion mandrel will encounter the clot material first. The slidable loop then slides distally until the coils form a double inverted cone-shaped configuration. The coils will overlap and thus give more support for the removal of large clots.

The biphasic coils are deployed similarly except that electric current or heat is used to form the coil configurations if the straight configuration is the natural shape. If the coil configuration is the natural shape, then the user stops applying electric current or heat and the coil configuration will reform.

The clot is then retrieved by translating the insertion mandrel along with the catheter proximally. When the clot capture coil is pulled proximally the clot becomes ensnared. Additionally, while pulling proximally on the insertion mandrel, the coil is rotated by rotating the insertion mandrel to transfix the clot by corkscrewing the clot into the coils. The viscoelastic properties of the clot allow the clot to be captured within the side coils and to be pulled down using the most distal coils as a capture cup. The clot can then be completely removed or released into a vessel that does not perfuse a critical organ such as an external carotid artery.

A particularly useful introducing catheter is illustrated in FIG. 11. The introducing catheter 110 is hollow with a single lumen and has a Y junction towards its proximal end. The introducing catheter is a standard commercially available introducing catheter. The introducing catheter has two ports, 112 and 114. Port 112 is in straight communication with the longitudinal axis of the introducing catheter and is useful for the insertion of the catheter 12, coil 30 and insertion mandrel 16 of the present invention. The other port, which is angled away form the longitudinal axis of the insertion catheter, is for the attachment to a suction line from a vacuum source. Located at the distal end 116 of the introducing catheter is a marker band 118 that can be located via radiographic means while the introducing catheter is being used.

In practice, the introducing catheter 110 is inserted through a large vessel and through the vascular system to a position near a clot in an occluded artery under fluoroscopic guidance. The catheter 12, is then inserted through port 112 and through the introducing catheter such that the distal end of the catheter 12 has passed the distal end 116 of the introducing catheter. The catheter 12 is then translated across the clot. The coil 30 and insertion mandrel 16 are then inserted into the catheter 12. The insertion mandrel is then translated through the catheter 12 until the coil 30 is deployed in the vessel. The insertion mandrel is then translated proximally to ensnare the clot within the coil and then the catheter, coil and clot are translated toward the distal end 116 of the introducing catheter 110. Once the clot and the coil are at the distal end 116, suction is applied via port 114 to suck part of the clot into the distal end 116. The suction helps to keep the clot within the coil. Then the introducing catheter 110, the catheter 12, the clot and the coil 30 are removed from the patient.

FIG. 12 illustrates the invention being used as a filter in the inferior vena cava of a patient with a venous thrombus in a lower limb. A commercially available introducing catheter 130 is advanced into a femoral vein 122 and into the inferior vena cava 128 below the heart 126. A catheter 12 is then advanced through the introducing catheter. The coil 120 and insertion mandrel 16 are then advanced through the catheter 12 and the coil 120 is deployed within the inferior vena cava. The coil 120 has a large diameter, around 20 mm to 30 mm, such that when deployed it fits snugly within the inferior vena cava. The coil acts as a filter wherein pieces of the thrombus become trapped in the coil instead of being transported to the lungs. The thrombic material can then be removed from the patient.

Foreign bodies are removed as described above except that the foreign body becomes ensnared in the clot capture coil instead of a clot. Due to the numerous coils, it is much easier to ensnare a foreign body than using a loop type device.

The following examples illustrate some of the uses of the invention. The examples are provided for illustration purposes and are not meant to limit the invention to the specific examples.

Example 1

The clot capture coil was clinically tested in pigs. In the first study a pig's femoral artery was isolated and a large commercially available introducing catheter was inserted into the femoral artery. Arterial blood was then withdrawn and allowed to clot in vitro.

An arterial catheter was then inserted through the introducing catheter and into the carotid artery. The coagulated arterial blood was then released into the carotid artery branches via the arterial catheter resulting in the formation of numerous emboli.

Angiography was used to locate the emboli. While performing angiography a microcatheter (outer diameter of 3 French and inner diameter of 1 French) was inserted into an occluded carotid artery using a guide wire for placement and standard microcatheter placement techniques. The microcatheter was advanced distally past the clot. The guide wire was then withdrawn from the microcatheter.

A shape memory clot capture coil connected to an insertion mandrel was then introduced into the microcatheter using a small introducer. The coil configuration was the type illustrated in FIG. 2a. Because the coil extends distally from the insertion mandrel a small introducing catheter had to be used to introduce the clot capture coil into the microcatheter. The insertion mandrel and the clot capture coil was inserted in a retrograde direction into the introducing catheter. The inner diameter of the introducing catheter was identical to the microcatheter. The clot capture coil became straight due to the superelastic properties of the coil and the small inner diameter of the introducer. Once the coil was completely within the introducer, the introducer was aligned with the microcatheter and the coil was inserted into the microcatheter in an anterograde direction.

The clot capture coil was slowly advanced to the distal end of the microcatheter by translating the insertion mandrel. As the insertion mandrel was advanced, the coil began to be expressed from the distal end of the microcatheter. As more and more of the coil was expressed, the coil deployed and returned to its natural resting coiled shape as in FIG. 2c.

The clot capture coil was then pulled proximally to ensnare the clot. While pulling proximally, the coil was rotated by rotating the insertion mandrel to transfix the clot by corkscrewing the clot into the coils. The clot was then completely removed from the pig by removing the microcatheter, insertion mandrel, and the clot within the clot capture coil from the pig's femoral artery.

Example 2

The procedure of Example 1 was repeated using the shape memory clot capture coil configuration illustrated in FIG. 3. The clot was successfully corkscrewed and ensnared and removed from the pig's occluded cerebral artery.

Example 3

The procedure of Example 1 was repeated using a shape memory clot capture coil as illustrated in FIG. 4. Because this embodiment has the coil extending proximally from the distal end of the insertion mandrel, the clot capture coil was directly inserted into the microcatheter without the use of a small introducer. A clot in an occluded carotid artery was ensnared in the coil and completely removed.

Thus, a clot capture coil is disclosed which allows for the removal of thromboembolic material and foreign bodies from a blood vessel. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A device for removing an obstruction from a blood vessel, comprising:
    a first catheter having a lumen;
    an obstruction retriever positioned within the lumen of the first catheter, the obstruction retriever having a solid, non-hollow, obstruction-engaging portion extending from an insertion element, the obstruction-engaging portion being an elongate element which is fixedly attached to the insertion element and extends from the insertion element to a free floating end, the obstruction retriever having substantially only one filament which extends to the free floating end, the obstruction-engaging portion being movable between a collapsed position and an expanded position, and being in the collapsed position when positioned in the lumen and being naturally biased toward the expanded position when positioned outside the lumen; wherein the obstruction-engaging portion is made of a superelastic material.

2. The device of claim 1, further comprising a second catheter, the first catheter extending through a lumen in the second catheter.

3. The device of claim 1, wherein the obstruction-engaging portion of the obstruction retriever has a helical shape.

4. The device of claim 1, wherein the obstruction-engaging portion of the obstruction retriever has coils having varying diameters along the length of the obstruction-engaging portion.

5. The device of claim 1, wherein the obstruction-engaging portion of the obstruction retriever is configured to be deployed distal to the obstruction and moved proximally to ensnare and dislodge the obstruction.

* * * * *